United States Patent [19]

McFarland

[11] 4,452,080

[45] Jun. 5, 1984

[54] CALCULATING APPARATUS AND METHOD

[76] Inventor: William W. McFarland, 4405 Pagoda, Hutchinson, Kans. 67501

[21] Appl. No.: 425,403

[22] Filed: Sep. 28, 1982

[51] Int. Cl.³ ............................................. G01N 29/04
[52] U.S. Cl. ........................................ 73/588; 73/620
[58] Field of Search ................. 73/588, 620, 627, 629, 73/633

[56] References Cited

U.S. PATENT DOCUMENTS 2,846,875  8/1958  Grabendörfer ...................... 73/620

FOREIGN PATENT DOCUMENTS 1922000  9/1977  Fed. Rep. of Germany ........ 73/627
1414865  9/1965  France .................................. 73/620

OTHER PUBLICATIONS

*Nondestructive Testing–Ultrasonic Testing*, Classroom Training Handbook CT-6-4, General Dynamics, Convair Div., San Diego, Ca., C. 1967, pp. 4-27 and 4-28.

*Primary Examiner*—Anthony V. Ciarlante
*Attorney, Agent, or Firm*—James W. McFarland

[57] ABSTRACT

Apparatus and method for calculating and displaying the location of a defect inside a test specimen which has been detected by angled, ultrasonic beam, nondestructive inspection techniques are disclosed.

28 Claims, 7 Drawing Figures

CALCULATING APPARATUS AND METHOD

BACKGROUND OF THE INVENTION

This invention relates to apparatus and method for calculating and displaying the location of an internal defect detected by nondestructive inspection techniques. More particularly, the invention relates to such apparatus and method in association with angled, ultrasonic inspection.

Nondestructive ultrasonic inspection techniques are commonly utilized in production situations for inspecting the internal portions of a specimen to locate potential defects therein. An example of use of such inspection techniques is for inspecting the internal quality of a weld joint, and a common technique for inspecting a weld joint includes utilization of angled, ultrasonic beam techniques. This inspection technique comprises utilization of an angled ultrasonic transducer which is capable of introducing an ultrasonic sound beam into the test specimen at a preselected angle relative thereto. The ultrasonic sound beam totally internally reflects within the material at opposing parallel surfaces thereof to travel within the material along a substantially sawtooth-configured path. The angle beam transducer acts not only as an ultrasonic sound wave source, but also as a microphone for detecting the echoed reflection of the sound beam when it encounters a defect in the test specimen, such as within the interior of the weld joint being inspected. The echoed reflection, of course, travels along the same sawtooth path back to the transducer and provides a signal, normally an electrical signal in the form of a display on a CRT tube, to give the operator information as to the total path length the sound wave traveled upon contacting the located defect. Upon detecting the defect, the operator also is provided with information as to the actual distance between the transducer and a reference point in the test specimen or the weld joint thereof. The operator is then faced with the problem of calculating the actual location of the detected defect relative to the weld joint area being inspected to provide meaningful information to production personnel.

Normally such calculation includes manual determination and display of the sawtooth path, taking into account the thickness of the material being inspected as well as the particular angle of introduction of the sound beam into the test specimen. After generating such a layout of the sawtooth path of the sound wave, the operator must then measure along the length of the sawtooth path to locate the point related to the readout received from the angled transducer as to the total distance the sound wave traveled prior to encountering the defect. After so determining the relative location of the defect the operator must then relate the location to the configuration of the weld joint to this determined location of the defect in order to determine the precise location of the detected defect relative to the weld joint area being inspected. Such prior art, relatively totally manual techniques are quite time-consuming and include continuous, repetitive calculations of the same nature tending to cause errors in the process. Accordingly, it will be apparent that it is relatively time-consuming and inaccurate to develop a separate, manual calculation and display for each detected defect taking into account the various parameters involved including the angle of the sound beam, the thickness of the test specimen, and the determination of which portion of the sawtooth curve the defect was detected upon.

Another prior art method of calculating a located defect includes an arrangement for determining the location of the detected defect relative to the thickness of the test specimen. However, this prior art arrangement, such as illustrated in "NONDESTRUCTIVE TESTING-ULTRASONIC TESTING", Classroom Training Handbook CT-6-4, General Dynamics, Convair Division, San Diego, Calif., Copyright 1967, pages 4-27 and 28, is usable only for one particular angle of sound beam introduction, has a limited capability with regard to accuracy and universality, and still requires the determination in a separate manner of the location of the defect within the weld area being inspected.

It is quite important in a production situation that the location of the defect relative to the weld joint being inspected be rapidly and accurately calculated. This provides information, for example, to reset a weld setup to eliminate the detected defect. More particularly, if the defect is located well within the interior of the weld joint this advises the weld operator that porosity has been detected. Specific information as to the location of such porosity will advise the operator on the best manner for readjusting the weld setup to eliminate the defect in subsequent welding operations. Similarly, if a defect is located in the joint area of the weld, this provides information that the defect is in the form of lack of fusion, telling the weld operator further information as to how to most rapidly eliminate the defect.

SUMMARY OF THE INVENTION

Accordingly, it is a broad object of the present invention to provide apparatus and method for rapidly and accurately calculating and displaying the location of a detected defect in relation to the configuration of a test specimen.

More particularly, an object of the invention is to provide a display of the location of the defect and a correlated display of the configuration of the test specimen, the defect being displayed in a first set of coordinates, and the configuration of the test specimen being displayed in overlying relation to the defect but in a second coordinate set which has preselected, scaled relationships to the first coordinate set.

Another object of the present invention is to provide apparatus and method for assisting and calculating the location of a detected defect and which is operable at a variety of sound beam angles.

Another more particular object of the invention is to provide apparatus and method of the type described in the foregoing objects which is readily and very accurately adjustable in relation to the thickness of the test specimen.

Another important object of the present invention is to provide apparatus and method of the type described, in which a plurality of skips, or sections of the sawtooth path of the sound path, can be displayed for more accurate and more reliable operation.

More particularly, the invention contemplates apparatus and method which includes a plurality of scales and movable plates disposed in overlying relationship with one another in order to permit display of the located defect and the configuration of the weld joint itself in overlying, correlated relationship to one another. The sound beam path and the location of a detected defect are displayed in a first set of coordinate systems, while the configuration of the test specimen is displayed in another set of coordinate system having a preselected relationship to the first coordinate system. More specifically, in a preferred embodiment wherein the coordinate systems utilized are Cartesian coordinates, the X coordinates are related to one another by a factor of Sin $\theta$, where $\theta$ is the angle of introduction of the sound beam, and the Y coordinates are related to one another by a scale factor of 2. In one embodiment of the present invention the distance through which the sound beam passed prior to detecting the defect is taken into account by utilization of a plurality of scales, one for each of the particular sound beam angles which may be utilized, while in another embodiment such determination is made by indicia included directly upon lines representing the sawtooth configuration of the sound beam path.

These and other objects and advantages of the present invention are more particularly set forth in the following detailed description of a preferred embodiment of the invention when read in conjunction with the accompanying drawings.

DETAILED DESCRIPTION OF THE PREFERRED EMBODIMENT

Figures 1, 6:
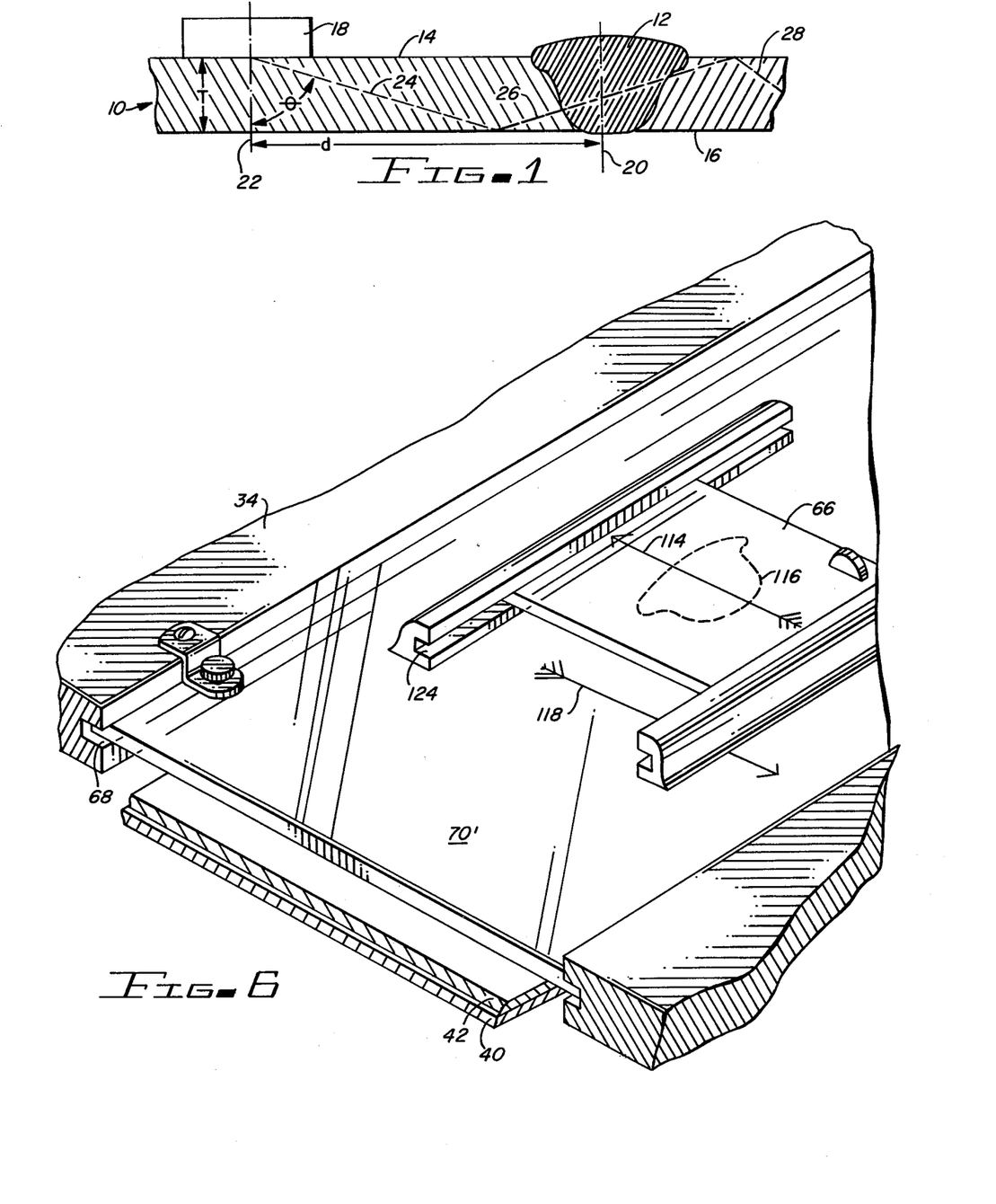
FIG. 1 is a partial elevational, cross-sectional view of a test specimen and angled ultrasonic sound beam non-destructive inspection apparatus being utilized therewith.
FIG. 6 is a partial, perspective view of an alternate arrangement for carrying the cursors utilized in the present invention.
Figure 2:
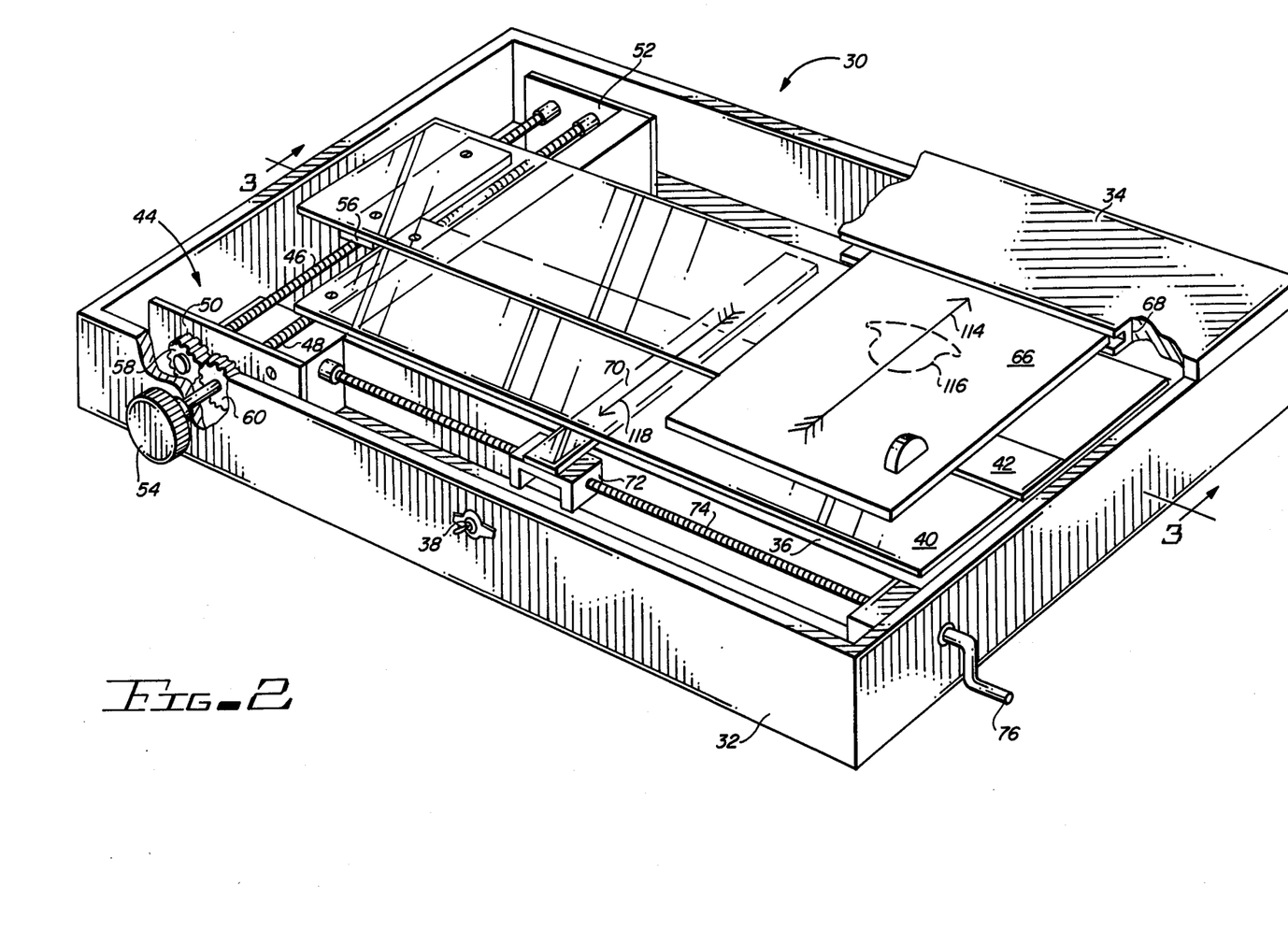
FIG. 2 is a perspective view of apparatus constructed in accordance with the principles of the present invention, with portions broken away to reveal internal details of construction.

Referring now more particularly to the drawings, illustrated in FIG. 1 is a typical test specimen 10 which may be the cross-sectional portion of a cylinder having a weld joint 12 intersecuring different portions of the cylinder. The test specimen is of a relative uniform thickness with a top reference surface 14 and a parallel lower surface 16. Schematically illustrated in conjunction with the test specimen 10 is an angled, ultrasonic beam transducer 18 which is operable to introduce an ultrasonic sound beam into the test specimen at a known location and at a known angle $\theta$. More particularly, the angled beam is introduced at a location which is related to a reference line 20 of the weld joint at a distance "d" therefrom. Similarly, the angle of introduction, $\theta$, is measured from a line 22 extending in a direction perpendicular to the reference surface 14. From the known parameters of thickness of the material "T", the angle $\theta$, and the known distance "d", which is recorded upon detecting a defect in the test specimen, the operator must calculate the location of the defect relative to the weld joint 12.

The ultrasonic angle transducer 18 is operable, as mentioned, to introduce a sound beam along a path in which the beam totally internally reflects between the surfaces 14 and 16 to define a sawtooth path configuration illustrated by dashed lines in FIG. 1. More particularly, the sawtooth path is commonly referred to as being made up of a plurality of "skips". The first skip is illustrated at line 24, the second skip illustrated by line 26 and the third skip illustrated by line 28.

Referring now more particularly to FIGS. 2-5, the present invention contemplates apparatus for calculating the location of the detected defect in relation to the weld joint area, the apparatus being generally denoted by the numeral 30. Apparatus 30 includes a rectangular housing 32 having a top cover 34 with a window area within the center area thereof. Apparatus 30 further includes a baseplate 36 which is securred in nonmoving realtionship to the housing. More particularly, the base plate 36 is translucent in nature and disposed above a light source (not shown) energized by an appropriate switch 38 on the exterior of the housing.

Figure 3:
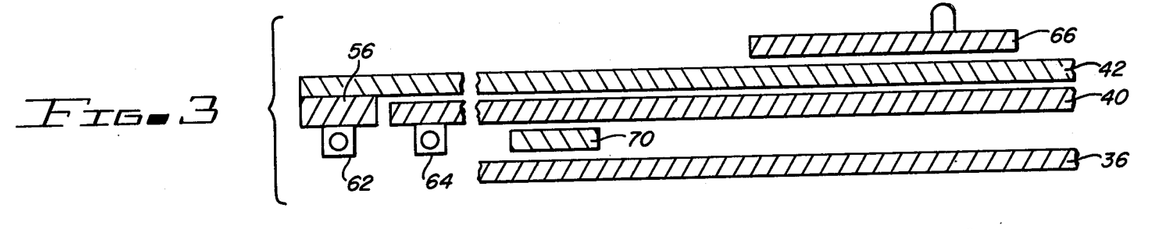
FIG. 3 is an elevational, partial, cross-sectional view of the device illustrated in FIG. 2 and as viewed generally along lines 3—3 of FIG. 2.

Within the housing and preferably disposed in overlying relationship to base plate 36 is a first movable transparent plate 40 and second movable transparent plate 42. Plates 40 and 42 are oppositely adjustable in a first, vertical direction generally by a drive means in the form of rotary screw drive 44. The rotary screw drive includes a pair of parallel, threaded drive shafts 46, 48 which are rotatably mounted to upstanding supports 50, 52 carried within the housing 30. The rotary drive further includes a pair of intermeshing or interengaging gears 58, 60 affixed to each of the shafts 46, 48. A rotary knob 54 is secured to shaft 48 and disposed exteriorly of the housing. The plates 40 and 42, as illustrated in FIG. 3, each have depending nut sections 62, 64 with associated threaded apertures therein which receive the respective drive shafts 46 and 48. Upon rotation of knob 54 the gears 58 and 60 rotate the shafts 46, 48 in opposite directions, and the threaded drive between the apertures of nuts 62 and 64 and the drive shafts causes the first and second plates 40, 42 to move in a vertical direction oppositely from one another an equal distance. As clearly illustrated in FIG. 3, a spacer plate 56 is disposed intermediate the nut 62 and the top of upper second plate 42 so as to space plate 42 a slight distance above the lower plate 40.

The drive means 44 permit extremely accurate location of plate 42 to plate 40 upon initial assembly of apparatus 30. The double step down drive afforded by the shaft to aperture 62, 64 as well as the interengaging teeth of gears 58, 60 assure very fine, vernier type adjustment of the vertical location of plate 42 upon shifting the drive connections between gears 58, 60 by a single tooth.

The apparatus further includes a first cursor 66 disposed above the first and second plates and movable horizontally in channel means on the housing such as the illustrated channel 68 within the top cover 34. The apparatus further includes a second cursor 70 disposed intermediate the base plate 36 and the first plate 40 so as to be movable horizontally in the same direction as the first cursor 66. In this respect, a drive for horizontally shifting the second cursor 70 includes a depending section 72 on the cursor having a threaded aperture receiving a threaded drive shaft 74 which is rotatably mounted within the housing. An external drive handle 76 is rotatable to rotate the shaft 74 and cause horizontal displacement of cursor 70 in relation to the direction of rotation of drive handle 76.

Figures 4, 5:
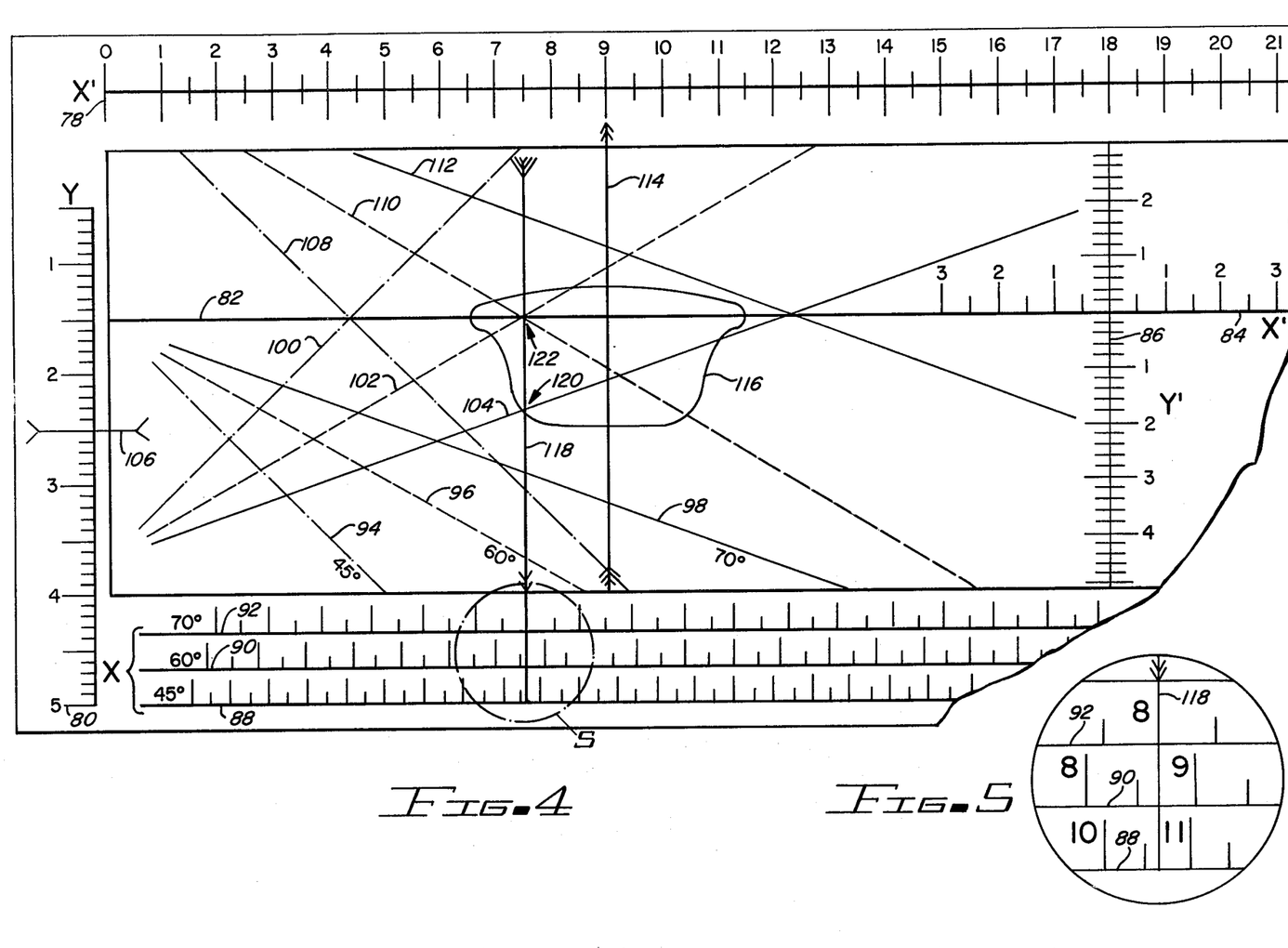
FIG. 4 is a partial plan view of the detailed scales and indicia carried on the apparatus of FIG. 1.
FIG. 5 is an enlarged detail view of the portion circled by lines 5—5 of FIG. 4.

Various indicia, scales and scribes are contained upon the base plate 36, first plate 40, second plate 42, first cursor 66, and second cursor 70, and are all illustrated in correlated relationship in FIG. 4. More particularly, the base plate 36 includes the following thereon: a first horizontal scale 78 having indicia thereon in a coordinate X' with the origin of scale 78 correlated to the known entry point of the sound beam into the test specimen; a second vertical scale 80 in coordinate Y; a horizontal base line 82 depicting the top reference surface 14 of the test specimen; a pair of intersecting horizontal and vertical bullseye scales 84, 86 respectively in coordinates X' and Y'; a plurality of third scales 88, 90, and 92 in coordinates X, one such scale being included for three different angles $\theta$ of value 45°, 60° and 70°; and a set of first skip lines 94, 96, and 98 emanating from the location of the base line 82 aligned with the origin of scale 78 at respective angles 45°, 60° and 70°. Skip lines 94, 96, 98, represent the first skip portion 24 of the sound beam path for three preselected angles of introduction of the sound beam. Preferably the scaled relationship of coordinates X and X' are such that $X = X' \sin \theta$, and coordinates Y and Y' are relatively scaled such that $Y = 2'$. That is, the scale of coordinate X is reduced from that of coordinate X' by a factor of $\sin \theta$, while the scale of coordinate Y is double the scale of coordinate Y'.

The first plate 40 includes the following thereon: a set of second skip lines 100, 102, and 104 respectively representing the second skip portion 26 of the sound beam path and disposed at an angle representing the reflection off the bottom surface 16, which will be at a respective angles of $180° - \theta$ from the vertical direction; and a horizontal index scribe 106 which registers with the second scale 80.

The second plate 42 includes the following thereon: a set of third skip lines 108, 110, and 112 which are disposed at angles of 45°, 60°, and 70° and are thus disposed at the same angles as the set of first skip lines 94, 96, and 98. However, to represent the third skip section 28 of the sound path the set of third skip lines 108, 110, and 112 are displaced vertically from the set of first skip lines 94, 96, 98.

The first cursor 66 includes a second index scribe 114 which registers with the first scale 78; and a surface area upon which is sketched or otherwise depicted a display 116 of the configuration of the weld joint area being tested or other appropriate configuration of the test specimen being inspected.

The second cursor 70 includes a third scribe thereon denoted by the numeral 118 which registers with the set of third scales 88, 90, and 92. FIG. 5 illustrates an enlarged portion showing the relationship of third scribe 118 to the indicia carried on the third scales 88, 90, and 92. The third index scribe 118 in combination with the third scales 88, 90, and 92 provide indicia means for cooperating with the various skip lines to locate the position of the detected defect in relation to the skip lines.

In operation, the operator of the equipment skims the angle transducer 18 back-and-forth across the reference surface 14 of the test specimen until a defect is located. The defect depiction of course is on a CRT display associated with the angle transducer as mentioned previously. The operator from the CRT display thus has information as to the actual distance the sound beam has traveled from the transducer to the defect, commonly referred to as the "sound path distance". Also, the operator knows the thickness "T" of the material, the angle $\theta$ which he has preselected to utilize with the testing procedure, and upon defect detection determines the distance "d" between the origin or known entry point of the sound path to a reference point such as illustrated by line 20 in FIG. 1 of the test specimen weld joint. With this information he then utilizes the apparatus 30 to locate the defect within the weld joint.

For example, the following hypothetical case is assumed for purposes of explanation: a defect is detected at a sound path distance of 8.0 in a test specimen whose material thickness "T" is 2.5 by use of a 70° angle transducer, the defect being located at a horizontal distance "d" of 9.0. To utilize apparatus 30, upon the surface of first cursor 66 the operator sketches the configuration of the weld joint, which is known such as by a blueprint thereof. Bullseye scales 84 and 86 are used to assist in accurately depicting the configuration of the test specimen relative to base line 82 (i.e. the reference surface 14) and in the coordinates X', Y', by aligning scribe 114 with scale 86. Upon sketching the display 116 the operator then adjusts first cursor 66 horizontally such that the second index scribe 114 registers with and is set upon first scale 78 at the horizontal distance "d" of 9.0. In this manner the display 116 of the configuration of the test specimen is located relative to the known entry point of the sound beam and in coordinates X' and Y'.

Next, the operator adjusts the first plate by rotation of knob 54 in relation to the material thickness "T". More particularly, the first plate is adjusted vertically until the first index scribe 106 is set upon second scale 80 to the known material thickness of 2.5. In this manner the set of second skip lines 100, 102, and 104 are located in coorelation to the thickness of the test specimen and in the coordinate Y. By virtue of the rotary screw drive 44, such positioning of plate 40 automatically positions the second plate 42 and the set of third skip lines 108, 110, 112 thereon. That the third set of skip lines are coorelated relative to the thickness of the material is readily determined by noting that the intersection of the set of second and third skip lines (i.e. intersection of lines 100 and 108, or lines 102 and 110, or lines 104 and 112) each align with and are juxtaposed directly upon base line 82 representing the top reference of the surface 14.

After the above-described adjustment of the first cursor 66 as a function of the horizontal distance "d", and the vertical adjustment of the plates 40 and 42 as a function of the material thickness "T", the operator then adjusts the second cursor 70 such that the third scribe 118 thereon registers with the set of third scales in relation to the measured sound path distance which has been obtained from the CRT display associated with the angle transducer. In the example given, therefore, second cursor 70 is adjusted horizontally until the scribe 118 intersects the indicia 8.0 on the scale 92 representing the 70° transducer being utilized.

Upon such location of the third index scribe 118, the actual location of the defect is represented by the intersection of index scribe 118 with the associated skip line of the 70° transducer. In the illustration of FIG. 4 this occurs at the intersection of lines 104 with scribe 118 at the noted point 120. The display 116 of the configuration of the test specimen is in correlated relationship to this location of the detected defect, and therefore the operator immediately surmises that the location of the detected defect lies at the joint line of the weld.

As another example of the versatility and utility of the present invention, the following situation is assumed: utilizing a 60° transducer a defect is detected at a sound path distance of 8.6 in a material of thickness "T" of 2.5 and at a horizontal distance "d" of 9.0. This hypothetical is also illustrated in FIG. 4. By going through the same process as discussed previously the location of the defect relative to the configuration of the test specimen is determined by intersection of third index scribe 118 with 60° line 102 at a point 122. Note that scribe 118 (see FIG. 5) is located at 8.6 on scale 90 utilized with the 60° transducer, while scribes 114 and 106 are respectively at 9.0 and 2.5. From this the operator can determine that the detected defect may be a spurious reading to advise him to recheck the defect for correctness. More particulary, it will be seen that the point 122 of the alleged defect appears to occur slightly past the supposed reflection of the sound beam between the second and third skips. This tells the operator that he may have received a spurious echo possibly relating to the top surface of the weld joint since such a reflection from the second to the third skip could not possibly occur here because the weld joint extends above surface 14 at this location. A recheck of the location of the defect is therefore advised. Such may be done by moving the transducer farther or closer to the weld joint to utilize a different skip section to locate the defect, or change to a different angle transducer to relocate the defect and to verify whether or not the reading is spurious or accurate.

From the foregoing it will be apparent that the present apparatus may be utilized to locate the detected defect extremely accurately relative to the weld joint and that the apparatus may be utilized for a plurality of different preselected angles θ, such as the illustrated 45°, 60°, and 70°, is readily adjustable for variation in material thickness "T", and has scales 78 and 80, 90, and 92 for directly adjusting the appropriate portions in relation to the noted distance "d" as well as the measured sound path distance. Accordingly, the apparatus provides a highly accurate calculating device for rapidly locating the detected defect to provide the maximum information available to production personnel for subsequently eliminating the defect. Due to the relationships of the coordinates X, Y to coordinates X', Y' the display of the test specimen can be shown in overlying relationship to the location of the detected defect to permit such rapid and accurate calculation.

From the foregoing it will be apparent that the present invention contemplates an improved method for displaying the location of the defect relative to the configuration of the test specimen by displaying, in coordinates X and Y, the path of the reflected sound wave, i.e. the skip lines, and the location of the detected defect (i.e. points 120 or 122 in the given examples) in relation to the entry point of the sound beam into the test specimen; and by displaying the configuration of the test specimen in coordinates X' and Y' in overlying relationship to the location of the detected defect, with the coordinates X and X' related to one another by a factor of Sin θ and the coordinates Y and Y' related to one another by a factor of 2. While the above apparatus has been illustrated in Cartesian coordinates X and Y it will be apparent that the present invention is equally useable in other coordinate systems also. For example, polar coordinates are expeditiously utilized for ring-like sections such as the plan cross-section of a cylinder. Thus, in more generalized terms the various scales included on the calculating apparatus 30 can be said to be in coordinates A and B and in coordinates A' and B', the respective coordinates related to one another in the following fashion: $A = 2A'$, and $B = B' \sin \theta$.

FIG. 6 illustrates a modified arrangement of the present invention wherein the second cursor 70 is configured as a larger plate 70' disposed above the second plate 42 and mounted within the channels 68 on the housing for horizontal movement to locate the third index scribe 118 in a manner discussed previously. The first cursor 66 in the FIG. 6 arrangement is disposed within channels 124 carried on top of the second cursor 70'. In this manner, the adjustment of the second cursor 70' to locate third index scribe 118 carries the first cursor 66 and its second index scribe 114 therewith. After locating the third index scribe 118, the first cursor 66 can be moved within channels 124 relative to cursor 70' to properly locate second index scribe 114. The alternative arrangement illustrated in FIG. 6 is generally operable because the location of the third index scribe relative to the second index scribe 114 on the calculating apparatus has been found to be sufficiently close to one another in any realistic situation so as to permit the first cursor 66 to be carried along with cursor 70', but yet independently movable therefrom for locating the second index scribe 114.

Figure 7:
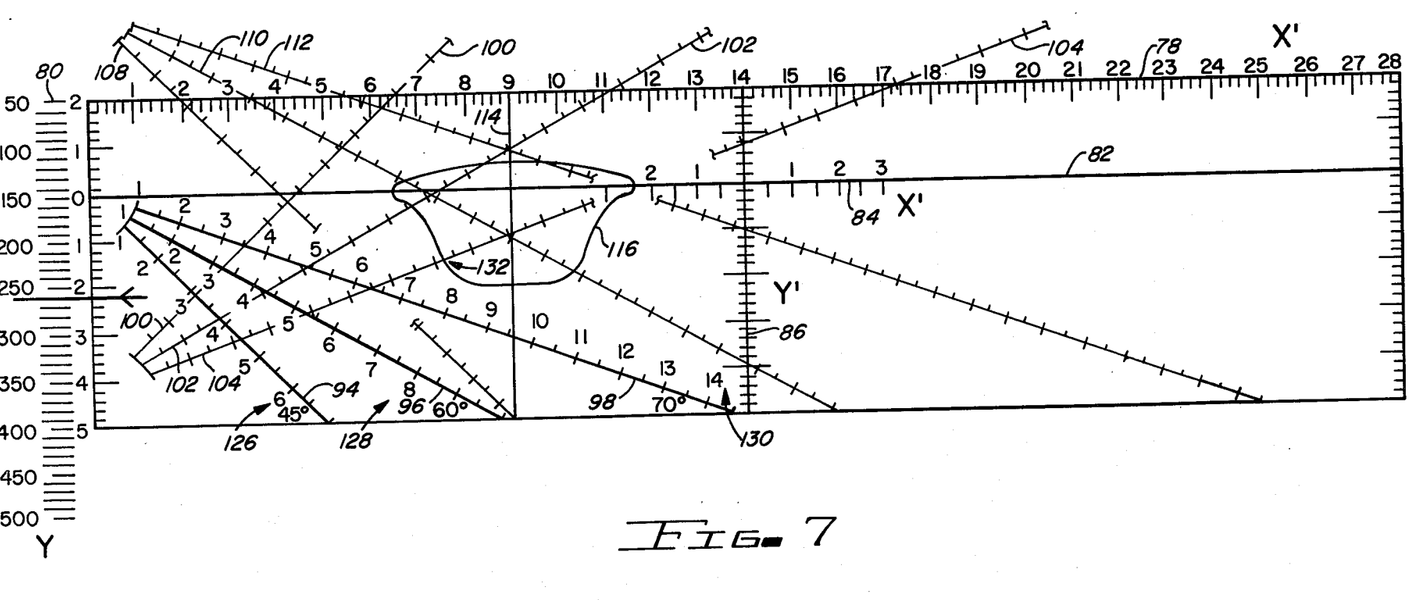
FIG. 7 is a view similar to FIG. 4 but showing an alternate arrangement for the scales and indicia utilized by the present invention.

FIG. 7 illustrates an alternate arrangement for the indicia means for locating the detected defect in relation to the sawtooth pattern. In FIG. 7, the three scales 88, 90, and 92 of FIG. 4 have been eliminated along with the third index scribe and second cursor 70. In place thereof the indicia means of FIG. 7 comprise indicia 126, 128, and 130 directly upon the first, second, and third skip lines. These indicia are effectively illustrated in the coordinates X inasmuch as the projection of these indicia onto the horizontal plane, i.e. onto scale 78 are such that they correspond to the relationship of $X = X' \sin \theta$. In utilization of the arrangement shown in FIG. 7, the detected sound path distance is found on the calculator by counting along the appropriate skip line relating to the angle transducer being utilized, up to the detected sound path distance.

Another distinction of the FIG. 7 arrangement in comparison to that shown in FIG. 4 is that the second plate which carries the skip lines 108, 110 and 112, is not connected in cooperating driving relationship with the drive mechanism which vertically adjusts the plate carrying the skip lines 100, 102, and 104. Rather, the second plate carrying the third skip lines is independently adjustable from the plate carrying the second skip lines. This permits the third skip lines normally to be shifted out of interference with the other skip lines when the third skip is not being utilized in the calculation. The third skip lines are located properly to the second skip lines when needed, by shifting the plate so that the intersection of the second and third skip lines align with base line 82. As illustrated in FIG. 7, the third skip lines are thus not in use.

As an example of the operation of FIG. 7 arrangement the following situation is assumed: a defect has been detected utilizing the 70° transducer at a sound path distance of 0.81 for a material whose thickness is 0.260, and at a location where the horizontal distance "d" is 0.90. Taking this information, the configuration of the weld joint is sketched upon the cursor carrying the second index scribe 118 in a manner noted previously utilizing the bullseye scales 84 and 86. The cursor then is shifted horizontally until the index scribe 114 registers with 0.9 on scale 78, coorelating the configuration of the test specimen 116 to the known entry point of the sound beam. The first plate 40 is adjusted vertically until the first index scribe 106 aligns with 0.260 on scale 80. This locates the second skip lines 100, 102, and 104 relative to the thickness "T" of the material. After these two steps, the operator then counts along 70° skip line 98, transferring to the reflecting second skip line 104, until he reaches 0.81 on the skip lines scales, noted as location 132 on line 104. Point 132 represents the location of the detected defect in relation to the configuration 116 of the test specimen.

The foregoing detailed description of the invention should be considered exemplary in nature and not as limiting to the scope and spirit of the invention as set forth in the appended claims. For example, electronic analogies to the calculations being performed are within the scope of the present invention to the extent they are defined in the claims herewith.

Having described the invention with sufficient clarity that those skilled in the art may make and use it, I claim:

1. Apparatus for determining the location of an internal defect in a test specimen of relatively uniform thickness, said defect being detected by the echoed reflection of a sound wave introduced into the test specimen at a known entry point on a reference surface thereof extending in a first direction, and at a known acute angle $\theta$ relative to a second direction perpendicular to said first direction, said apparatus comprising:
    a housing;
    a base plate secured to said housing and having a base line thereon extending in said first direction, a first scale extending in said first direction with an origin representing said known entry point and with indicia thereon in a coordinate X', a second scale extending in said second direction with indicia thereon in a coordinate Y, and a first skip line emanating relative to said origin at said angle $\theta$;
    a first plate overlying said base plate and adjustable in said second direction, said first plate having a second skip line thereon extending at an angle of $180° - \theta$, and further having a first index scribe registering with and settable on said second scale by adjustment of said first plate to locate said second skip line in correlation to said thickness of the test specimen;
    indicia means in a coordinate X cooperating with said first and second skip lines for locating the position of the detected defect in relation to said first and second skip lines, said coordinates X and X' being related to one another by a factor of substantially $\sin \theta$; and
    a first cursor overlying said first plate and adjustable in said first direction, said first cursor having thereon a display of the configuration of said test specimen in coordinates X' and Y' and at a location related to said base line, said coordinates Y and Y' being related to one another by a factor of substantially 2, said first cursor further having a second index scribe thereon registering with and settable on said first scale by adjustment of said cursor to locate said display of the configuration of the test specimen in correlation to said origin.

2. Apparatus as set forth in claim 1, wherein said indicia means comprise indicia on said first and second skip lines.

3. Apparatus as set forth in claim 1, wherein said indicia means comprise a third scale on said base plate extending in said first direction and having indicia thereon in coordinate X, and a second cursor movable in said first direction and having a third index scribe thereon registering with and settable on said third scale to locate the intersection of said third scribe with said skip lines in correlation to said location of the detected defect.

4. Apparatus as set forth in claim 3, wherein said second cursor is disposed intermediate said base plate and said first plate.

5. Apparatus as set forth in claim 3, further including a rotary screw drive for moving said second cursor in said first direction.

6. Apparatus as set forth in claim 5, wherein said rotary screw drive includes a threaded drive shaft rotatably mounted to said housing and received within a threaded aperture on said second cursor, and a drive handle secured to said drive shaft and located exteriorly of said housing.

7. Apparatus as set forth in claim 3, wherein said second cursor is disposed intermediate said first plate and said first cursor.

8. Apparatus as set forth in claim 7, wherein said housing includes channel means extending in said first direction and receiving said second cursor permitting adjustment thereof in said first direction.

9. Apparatus as set forth in claim 8, wherein said second cursor includes channel means extending in said first direction for receiving said first cursor whereby said first cursor is movable with said second cursor and movable independently of said second cursor.

10. Apparatus as set forth in claim 3, further including a second plate intermediate said first plate and said first cursor and also adjustable in said second direction, said second plate having a third skip line thereon extending at said angle $\theta$ and displaced from said first skip line in said second direction, said second plate adjustable relative to said first plate to locate said third skip line in correlation to said second skip line and said thickness of the material.

11. Apparatus as set forth in claim 10, wherein said second cursor is disposed intermediate said second plate and said first cursor.

12. Apparatus as set forth in claim 11, wherein said housing includes channel means extending in said first direction and receiving said second cursor for permitting adjustment thereof in said first direction.

13. Apparatus as set forth in claim 12, wherein said second cursor includes channel means extending in said first direction for receiving said first cursor whereby said first cursor is movable with said second cursor and movable independently of said second cursor.

14. Apparatus as set forth in claim 1, wherein said base plate has a set of first skip lines extending at various values of angle $\theta$, and said first plate has a set of second skip lines enxtending at correlated various values of $180° - \theta$, to permit use of said apparatus at said various values of $\theta$.

15. Apparatus as set forth in claim 1, further including a second plate intermediate said first plate and said first cursor and also adjustable in said second direction, said second plate having a third skip line thereon extending at said angle $\theta$ and displaced from said first skip line in said second direction, said second plate adjustable relative to said first plate to locate said third skip line in correlation to said second skip line and said thickness of the material.

16. Apparatus as set forth in claim 15, wherein said baseplate has a set of first skip lines extending at various values of said angle $\theta$, said first plate has a set of second skip lines extending at correlated various values of $180° - \theta$, and said second plate has a set of third skip lines extending at said various values of angle $\theta$, to permit use of said apparatus at said various values of $\theta$, said set of third skip lines being displaced from said set of first skip lines in said second direction.

17. Apparatus as set forth in claim 15, wherein said second plate is adjustable in said second direction independent of adjustment of said first plate to align the intersection of said second and third skip lines with said base line.

18. Apparatus as set forth in claim 15, further including drive means for simultaneously adjusting said first and second plates, said drive means operable to move said first and second plates oppositely from one another, said first and second plates relatively located with the intersection of said second and third skip lines aligning with said base line.

19. Apparatus as set forth in claim 18, wherein said drive means comprise a rotary screw drive engaging said first and second plates.

20. Apparatus as set forth in claim 19, wherein said rotary screw drive comprises a pair of parallel threaded drive shafts rotatably mounted on said housing and respectively received in threaded apertures on said first and second plates, and interengaging gears on said drive shafts for moving said first and second plates relatively oppositely upon rotation of one of said drive shafts.

21. Apparatus as set forth in claim 20, wherein said rotary screw drive further includes a rotatable knob secured to said one of the drive shafts and disposed exteriorly of said housing.

22. Apparatus as set forth in claim 1, wherein said housing includes channel means extending in said first direction and receiving said cursor for permitting adjustment thereof in said first direction.

23. Apparatus as set forth in claim 1, wherein said base plate includes intersecting bullseye scales extending in said first and second directions and have indicia thereon respectively in said coordinates X' and Y', said first cursor movable into overlying relationship to said bullseye scales to assist in displaying said configuration of the test specimen on said first cursor in said coordinates X' and Y'.

24. A calculator for determining the location of an internal defect within a test specimen of relatively uniform thickness wherein the defect has been detected by directing an angled, internal reflection, ultrasonic beam into the test specimen at any one of a plurality of preselected angles $\theta$ and at a known entry point for reflecting internally within the test specimen along a sawtooth path between opposing surfaces of the specimen, said calculator comprising:
  a housing;
  a base plate secured to the housing and having a first horizontal distance scale in coordinate X', a set of second horizontal distance scales corresponding to said plurality of angles $\theta$ and in coordinate X, where $X = X' \sin \theta$, intersecting horizontal and vertical bullseye scales in coordinates X' and Y', a vertical distance scale in coordinate Y, where $Y = 2Y'$, and a set of first skip lines extending respectively at each of said plurality of angles $\theta$;
  a first plate overlying said baseplate and movable vertically, said first plate having a set of second skip lines extending respectively at each of said plurality of angles $180 - \theta$, and an index scribe registering with and settable on said vertical distance scale in correlation to said thickness of the text specimen;
  a second plate overlying said baseplate and movable vertically relative to said first plate, said second plate having a set of third skip lines extending respectively at each of said plurality of angles $\theta$, said second plate vertically positionable in correlation to said thickness of the test specimen;
  a first cursor overlying said first and second plates and movable horizontally, said first cursor having a display of the configuration of said test specimen thereon and being movable horizontally to position said display in correlation to said known entry point, said first cursor having a second index scribe thereon registering with and settable on said first horizontal distance scale in correlation to said known entry point; and
  a second cursor movable horizontally and having a third index scribe thereon registering with and settable on said set of second horizontal distance scales to locate the intersection of said third index scribe with said first, second, and third sets of skip lines in correlation to the location of the detected defect.

25. Apparatus for displaying the location of a defect detected within a test specimen of relatively uniform thickness by use of angled, internal reflection, sound wave techniques which include directing a sound wave into the specimen at an angle $\theta$ and at a known entry point for reflecting internally within the specimen, said apparatus comprising:
  means for displaying, in coordinates A and B, the path of the reflected sound wave within the specimen and the location of the detected defect in relation to said entry point; and
  means for displaying said test specimen in coordinates A' and B' and in overlying relationship to said display of the location of the defect, said coordinates A and A' being related to one another by a factor of substantially 2 and said coordinates B and B' being related to one another by a factor of substantially $\sin \theta$, whereby said display of the test specimen and said display of the location of the defect are relatively correlated to one another.

26. Apparatus as set forth in claim 25, wherein said thickness of the specimen is displayed in said A' coordinate, and wherein $A = 2A'$ and $B = B' \sin \theta$.

27. Apparatus as set forth in claim 25, wherein said coordinate A, A' and B, B' are Cartesian coordinates, said thickness of the specimen being displayed in said A' coordinate, and wherein $A = 2A'$ and $B = B' \sin \theta$.

28. A method for displaying the location of a defect detected within a test specimen of relatively uniform thickness by use of angled, internal reflection, sound wave techniques which include directing a sound wave into the specimen at an angle $\theta$ and at a known entry point for reflecting internally within the specimen, said method comprising:
  displaying, in coordinates A and B, the path of the reflected sound wave within the specimen and the location of the detected defect in relation to said entry point; and displaying said test specimen in coordinates A' and B' and in overlying relationship to said display of the location of the defect, said coordinates A and A' being related to one another by a factor of substantially 2 and said coordinates B and B' being related to one another by a factor of substantially Sin $\theta$, whereby said display of the test specimen and said display of the location of the defect are relatively correlated to one another.

* * * * *